(12) United States Patent
Cuppoletti et al.

(10) Patent No.: US 7,354,720 B2
(45) Date of Patent: Apr. 8, 2008

(54) LABEL FREE ANALYSIS OF NUCLEIC ACIDS

(75) Inventors: Andrea Cuppoletti, Livermore, CA (US); Handong Li, San Jose, CA (US)

(73) Assignee: Affymetrix, Inc., Santa Clara, CA (US)

( * ) Notice: Subject to any disclaimer, the term of this patent is extended or adjusted under 35 U.S.C. 154(b) by 157 days.

(21) Appl. No.: 11/313,874

(22) Filed: Dec. 20, 2005

(65) Prior Publication Data

US 2006/0147965 A1    Jul. 6, 2006

Related U.S. Application Data

(60) Provisional application No. 60/640,385, filed on Dec. 30, 2004.

(51) Int. Cl.
*C12Q 1/68* (2006.01)
*C07H 21/02* (2006.01)
*C07H 21/04* (2006.01)

(52) U.S. Cl. .................. 435/6; 526/23.1; 526/24.3

(58) Field of Classification Search .............. 435/6; 536/23.1, 24.3
See application file for complete search history.

(56) References Cited

U.S. PATENT DOCUMENTS

| 2003/0148335 A1* | 8/2003 | Shen et al. ............... 435/6 |
| 2003/0207312 A1* | 11/2003 | Sorge ..................... 435/6 |
| 2005/0112770 A1* | 5/2005 | Nakamura et al. ......... 436/94 |
| 2005/0130174 A1* | 6/2005 | Bao et al. ................ 435/6 |
| 2006/0078925 A1* | 4/2006 | Mourelatos et al. ........ 435/6 |

* cited by examiner

*Primary Examiner*—Ethan Whisenant
(74) *Attorney, Agent, or Firm*—Cooley Godward Kronish LLP

(57) ABSTRACT

A method is provided for label free analysis of nucleic acid materials. In accordance with the present invention, a fluorescent material is provided having a certain fluorescence emission without nucleic acids attached thereto. The fluorescent material of the present invention, has a greater emission upon the binding of a single stranded nucleic acid and an even greater emission upon the binding of a double stranded nucleic acid allowing detection of double stranded binding without using a label attached to the DNA.

22 Claims, No Drawings

LABEL FREE ANALYSIS OF NUCLEIC ACIDS

FIELD OF THE INVENTION

The present invention relates to the detection of nucleic acids. More particularly, the present invention relates to the detection of double stranded nucleic acid hybridization without the use of any type of label attached to the nucleic acid.

BACKGROUND OF THE INVENTION

Since virtually the inception of molecular biology, the detection of nucleic acids (both DNA and RNA) has turned on the incorporation of various labels into these molecules. At first, radioactive labels such as $^{32}P$ were widely using in southerns, northerns and sequencing. Later, a great number of non-radioactive labels were developed, having groups which either fluoresced themselves or fluoresced upon interactions with a second molecule (e.g. biotin). It is an object of the present invention to develop methods and instruments which are capable of detecting nucleic acids without introduction of any type of exogenous label.

SUMMARY OF THE INVENTION

In accordance with an aspect of the present invention, a method for detecting label free analysis of nucleic acid binding is presented, the method having the steps of providing a fluorescent polymeric matrix having a first fluorescent emission intensity; attaching a single stranded DNA or RNA species to said fluorescent matrix to provide a second, greater fluorescent intensity; and hybridizing said single stranded RNA or DNA to a homologous nucleic acid, causing a further increase in said fluorescent intensity, allowing detection of said hybridization of said homologous nucleic acid binding.

DETAILED DESCRIPTION OF THE INVENTION

A. General

The present invention has many preferred embodiments and relies on many patents, applications and other references for details known to those of the art. Therefore, when a patent, application, or other reference is cited or repeated below, it should be understood that it is incorporated by reference in its entirety for all purposes as well as for the proposition that is recited.

As used in this application, the singular form "a," "an," and "the" include plural references unless the context clearly dictates otherwise. For example, the term "an agent" includes a plurality of agents, including mixtures thereof.

An individual is not limited to a human being but may also be other organisms including but not limited to mammals, plants, bacteria, or cells derived from any of the above.

Throughout this disclosure, various aspects of this invention can be presented in a range format. It should be understood that the description in range format is merely for convenience and brevity and should not be construed as an inflexible limitation on the scope of the invention. Accordingly, the description of a range should be considered to have specifically disclosed all the possible subranges as well as individual numerical values within that range. For example, description of a range such as from 1 to 6 should be considered to have specifically disclosed subranges such as from 1 to 3, from 1 to 4, from 1 to 5, from 2 to 4, from 2 to 6, from 3 to 6 etc., as well as individual numbers within that range, for example, 1, 2, 3, 4, 5, and 6. This applies regardless of the breadth of the range.

The practice of the present invention may employ, unless otherwise indicated, conventional techniques and descriptions of organic chemistry, polymer technology, molecular biology (including recombinant techniques), cell biology, biochemistry, and immunology, which are within the skill of the art. Such conventional techniques include polymer array synthesis, hybridization, ligation, and detection of hybridization using a label. Specific illustrations of suitable techniques can be had by reference to the example herein below. However, other equivalent conventional procedures can, of course, also be used. Such conventional techniques and descriptions can be found in standard laboratory manuals such as *Genome Analysis: A Laboratory Manual Series (Vols. I-IV)*, *Using Antibodies: A Laboratory Manual, Cells: A Laboratory Manual, PCR Primer: A Laboratory Manual*, and *Molecular Cloning: A Laboratory Manual* (all from Cold Spring Harbor Laboratory Press), Stryer, L. (1995) *Biochemistry* (4th Ed.) Freeman, New York, Gait, "Oligonucleotide Synthesis: A Practical Approach" 1984, IRL Press, London, Nelson and Cox (2000), *Lehninger, Principles of Biochemistry* $3^{rd}$ Ed., W.H. Freeman Pub., New York, N.Y. and Berg et al. (2002) *Biochemistry*, $5^{th}$ Ed., W.H. Freeman Pub., New York, N.Y., all of which are herein incorporated in their entirety by reference for all purposes.

The present invention can employ solid substrates, including arrays in some preferred embodiments. Methods and techniques applicable to polymer (including protein) array synthesis have been described in U.S. Ser. No. 09/536,841, WO 00/58516, U.S. Pat. Nos. 5,143,854, 5,242,974, 5,252,743, 5,324,633, 5,384,261, 5,405,783, 5,424,186, 5,451,683, 5,482,867, 5,491,074, 5,527,681, 5,550,215, 5,571,639, 5,578,832, 5,593,839, 5,599,695, 5,624,711, 5,631,734, 5,795,716, 5,831,070, 5,837,832, 5,856,101, 5,858,659, 5,936,324, 5,968,740, 5,974,164, 5,981,185, 5,981,956, 6,025,601, 6,033,860, 6,040,193, 6,090,555, 6,136,269, 6,269,846 and 6,428,752, in PCT Applications Nos. PCT/US99/00730 (International Publication No. WO 99/36760) and PCT/US01/04285 (International Publication No. WO 01/58593), which are all incorporated herein by reference in their entirety for all purposes.

Patents that describe synthesis techniques in specific embodiments include U.S. Pat. Nos. 5,412,087, 6,147,205, 6,262,216, 6,310,189, 5,889,165, and 5,959,098. Nucleic acid arrays are described in many of the above patents, but the same techniques are applied to polypeptide arrays.

Nucleic acid arrays that are useful in the present invention include those that are commercially available from Affymetrix (Santa Clara, Calif.) under the brand name GeneChip®. Example arrays are shown on the website at affymetrix.com.

The present invention also contemplates many uses for polymers attached to solid substrates. These uses include gene expression monitoring, profiling, library screening, genotyping and diagnostics. Gene expression monitoring and profiling methods can be shown in U.S. Pat. Nos. 5,800,992, 6,013,449, 6,020,135, 6,033,860, 6,040,138, 6,177,248 and 6,309,822. Genotyping and uses therefore are shown in U.S. Ser. Nos. 10/442,021, 10/013,598 (U.S. Patent Application Publication 20030036069), and U.S. Pat. Nos. 5,856,092, 6,300,063, 5,858,659, 6,284,460, 6,361,947, 6,368,799 and 6,333,179. Other uses are embodied in U.S. Pat. Nos. 5,871,928, 5,902,723, 6,045,996, 5,541,061, and 6,197,506.

The present invention also contemplates sample preparation methods in certain preferred embodiments. Prior to or concurrent with genotyping, the genomic sample may be amplified by a variety of mechanisms, some of which may employ PCR. See, for example, *PCR Technology: Principles and Applications for DNA Amplification* (Ed. H. A. Erlich, Freeman Press, NY, N.Y., 1992); *PCR Protocols: A Guide to Methods and Applications* (Eds. Innis, et al., Academic Press, San Diego, Calif., 1990); Mattila et al., *Nucleic Acids Res.* 19, 4967 (1991); Eckert et al., *PCR Methods and Applications* 1, 17 (1991); *PCR* (Eds. McPherson et al., IRL Press, Oxford); and U.S. Pat. Nos. 4,683,202, 4,683,195, 4,800,159 4,965,188,and 5,333,675, and each of which is incorporated herein by reference in their entireties for all purposes. The sample may be amplified on the array. See, for example, U.S. Pat. No. 6,300,070 and U.S. Ser. No. 09/513,300, which are incorporated herein by reference.

Other suitable amplification methods include the ligase chain reaction (LCR) (for example, Wu and Wallace, *Genomics* 4, 560 (1989), Landegren et al., *Science* 241, 1077 (1988) and Barringer et al. *Gene* 89:117 (1990)), transcription amplification (Kwoh et al., *Proc. Natl. Acad. Sci. USA* 86, 1173 (1989) and WO88/10315), self-sustained sequence replication (Guatelli et al., *Proc. Nat. Acad. Sci. USA,* 87, 1874 (1990) and WO90/06995), selective amplification of target polynucleotide sequences (U.S. Pat. No. 6,410,276), consensus sequence primed polymerase chain reaction (CP-PCR) (U.S. Pat. No. 4,437,975), arbitrarily primed polymerase chain reaction (AP-PCR) (U.S. Pat. Nos. 5,413,909, 5,861,245) and nucleic acid based sequence amplification (NABSA). (See, U.S. Pat. Nos. 5,409,818, 5,554,517, and 6,063,603, each of which is incorporated herein by reference). Other amplification methods that may be used are described in, U.S. Pat. Nos. 5,242,794, 5,494,810, 4,988,617 and in U.S. Ser. No. 09/854,317, each of which is incorporated herein by reference.

Additional methods of sample preparation and techniques for reducing the complexity of a nucleic sample are described in Dong et al., *Genome Research* 11, 1418 (2001), in U.S. Pat. Nos. 6,361,947, 6,391,592 and U.S. Ser. Nos. 09/916,135, 09/920,491 (U.S. Patent Application Publication 20030096235), Ser. No. 09/910,292 (U.S. Patent Application Publication 20030082543), and Ser. No. 10/013,598.

Methods for conducting polynucleotide hybridization assays have been well developed in the art. Hybridization assay procedures and conditions will vary depending on the application and are selected in accordance with the general binding methods known including those referred to in: Maniatis et al. *Molecular Cloning: A Laboratory Manual* (2$^{nd}$ Ed. Cold Spring Harbor, N.Y, 1989); Berger and Kimmel *Methods in Enzymology,* Vol. 152, *Guide to Molecular Cloning Techniques* (Academic Press, Inc., San Diego, Calif., 1987); Young and Davism, *P.N.A.S,* 80: 1194 (1983). Methods and apparatus for carrying out repeated and controlled hybridization reactions have been described in U.S. Pat. Nos. 5,871,928, 5,874,219, 6,045,996 and 6,386,749, 6,391,623 each of which are incorporated herein by reference The present invention also contemplates signal detection of hybridization between ligands in certain preferred embodiments. See U.S. Pat. Nos. 5,143,854, 5,578,832; 5,631,734; 5,834,758; 5,936,324; 5,981,956; 6,025,601; 6,141,096; 6,185,030; 6,201,639; 6,218,803; and 6,225,625, in U.S. Ser. No. 10/389,194 and in PCT Application PCT/US99/06097 (published as WO99/47964), each of which also is hereby incorporated by reference in its entirety for all purposes.

Methods and apparatus for signal detection and processing of intensity data are disclosed in, for example, U.S. Pat. Nos. 5,143,854, 5,547,839, 5,578,832, 5,631,734, 5,800, 992, 5,834,758; 5,856,092, 5,902,723, 5,936,324, 5,981, 956, 6,025,601, 6,090,555, 6,141,096, 6,185,030, 6,201, 639; 6,218,803; and 6,225,625, in U.S. Ser. Nos. 10/389, 194, 60/493,495 and in PCT Application PCT/US99/06097 (published as WO99/47964), each of which also is hereby incorporated by reference in its entirety for all purposes.

The practice of the present invention may also employ conventional biology methods, software and systems. Computer software products of the invention typically include computer readable medium having computer-executable instructions for performing the logic steps of the method of the invention. Suitable computer readable medium include floppy disk, CD-ROM/DVD/DVD-ROM, hard-disk drive, flash memory, ROM/RAM, magnetic tapes and etc. The computer executable instructions may be written in a suitable computer language or combination of several languages. Basic computational biology methods are described in, for example Setubal and Meidanis et al., *Introduction to Computational Biology Methods* (PWS Publishing Company, Boston, 1997); Salzberg, Searles, Kasif, (Ed.), *Computational Methods in Molecular Biology,* (Elsevier, Amsterdam, 1998); Rashidi and Buehler, *Bioinformatics Basics: Application in Biological Science and Medicine* (CRC Press, London, 2000) and Ouelette and Bzevanis *Bioinformatics: A Practical Guide for Analysis of Gene and Proteins* (Wiley & Sons, Inc., 2$^{nd}$ ed., 2001). See U.S. Pat. No. 6,420,108.

The present invention may also make use of various computer program products and software for a variety of purposes, such as probe design, management of data, analysis, and instrument operation. See, U.S. Pat. Nos. 5,593,839, 5,795,716, 5,733,729, 5,974,164, 6,066,454, 6,090,555, 6,185,561, 6,188,783, 6,223,127, 6,229,911 and 6,308,170.

Additionally, the present invention may have preferred embodiments that include methods for providing genetic information over networks such as the Internet as shown in U.S. Ser. Nos. 10/197,621, 10/063,559 (United States Publication No. 20020183936), Ser. Nos. 10/065,856, 10/065, 868, 10/328,818, 10/328,872, 10/423,403, and 60/482,389.

B. Definitions

The term "array" as used herein refers to an intentionally created collection of molecules which can be prepared either synthetically or biosynthetically. The molecules in the array can be identical or different from each other. The array can assume a variety of formats, for example, libraries of soluble molecules; libraries of compounds tethered to resin beads, silica chips, or other solid supports.

The term "monomer" as used herein refers to a single unit of polymer, which can be linked with the same or other monomers to form a biopolymer (for example, a single amino acid or nucleotide with two linking groups one or both of which may have removable protecting groups) or a single unit which is not part of a biopolymer. Thus, for example, a nucleotide is a monomer within an oligonucleotide polymer, and an amino acid is a monomer within a protein or peptide polymer; antibodies, antibody fragments, chromosomes, plasmids, mRNA, cRNA, tRNA etc., for example, are also polymers.

The term "biopolymer" or sometimes refer by "biological polymer" as used herein is intended to mean repeating units of biological or chemical moieties. Representative biopolymers include, but are not limited to, nucleic acids, oligonucleotides, amino acids, proteins, peptides, hormones, oligosaccharides, lipids, glycolipids, lipopolysaccharides, phospholipids, synthetic analogues of the foregoing, including, but not limited to, inverted nucleotides, peptide nucleic acids, Meta-DNA, and combinations of the above. It is important to note that biopolymers and polymers are not mutually exclusive. Proteins, enzymes, DNA, polyethylene, RNA, are all polymers as they are derived from a repeating monomer units. However, proteins, enzymes, DNA are all biopolymers as many of them first appeared in nature. Sometimes, it is not easy to classify something as a biopolymer or a polymer. For example, vast number of human made amino acid derivatives and nucleotide derivatives have been created and polymerized. Some of these are based on natural products, many more are not. At this point the distinction between the two can be somewhat semantical.

The term "biopolymer synthesis" as used herein is intended to encompass the synthetic production, both in situ (in the cell) and synthetically, e.g. by organic synthetic techniques outside of the cell, of a biopolymer. Related to a bioploymer is a "biomonomer".

The term "combinatorial synthesis strategy" as used herein refers to a combinatorial synthesis strategy is an ordered strategy for parallel synthesis of diverse polymer sequences by sequential addition of reagents which may be represented by a reactant matrix and a switch matrix, the product of which is a product matrix. A reactant matrix is a l column by m row matrix of the building blocks to be added. The switch matrix is all or a subset of the binary numbers, preferably ordered, between l and m arranged in columns. A "binary strategy" is one in which at least two successive steps illuminate a portion, often half, of a region of interest on the substrate. In a binary synthesis strategy, all possible compounds which can be formed from an ordered set of reactants are formed. In most preferred embodiments, binary synthesis refers to a synthesis strategy which also factors a previous addition step. For example, a strategy in which a switch matrix for a masking strategy halves regions that were previously illuminated, illuminating about half of the previously illuminated region and protecting the remaining half (while also protecting about half of previously protected regions and illuminating about half of previously protected regions). It will be recognized that binary rounds may be interspersed with non-binary rounds and that only a portion of a substrate may be subjected to a binary scheme. A combinatorial "masking" strategy is a synthesis which uses light or other spatially selective deprotecting or activating agents to remove protecting groups from materials for addition of other materials such as amino acids.

The term "complementary" as used herein refers to the hybridization or base pairing between nucleotides or nucleic acids, such as, for instance, between the two strands of a double stranded DNA molecule or between an oligonucleotide primer and a primer binding site on a single stranded nucleic acid to be sequenced or amplified. Complementary nucleotides are, generally, A and T (or A and U), or C and G. Two single stranded RNA or DNA molecules are said to be complementary when the nucleotides of one strand, optimally aligned and compared and with appropriate nucleotide insertions or deletions, pair with at least about 80% of the nucleotides of the other strand, usually at least about 90% to 95%, and more preferably from about 98 to 100%. Alternatively, complementarity exists when an RNA or DNA strand will hybridize under selective hybridization conditions to its complement. Typically, selective hybridization will occur when there is at least about 65% complementary over a stretch of at least 14 to 25 nucleotides, preferably at least about 75%, more preferably at least about 90% complementary. See, M. Kanehisa Nucleic Acids Res. 12:203 (1984), incorporated herein by reference.

The term "copolymer" refers to a polymer that is composed of more than one monomer. Copolymers may be prepared by polymerizing one or more monomers to provide a copolymer.

The term "detectable moiety" (Q) means a chemical group that provides a signal. The signal is detectable by any suitable means, including spectroscopic, photochemical, biochemical, immunochemical, electrical, optical or chemical means. In certain cases, the signal is detectable by 2 or more means.

The detectable moiety provides the signal either directly or indirectly. A direct signal is produced where the labeling group spontaneously emits a signal, or generates a signal upon the introduction of a suitable stimulus. Radiolabels, such as $^3$H, $^{125}$I, $^{35}$S, $^{14}$C or $^{32}$P, and magnetic particles, such as Dynabeads™, are nonlimiting examples of groups that directly and spontaneously provide a signal. Labeling groups that directly provide a signal in the presence of a stimulus include the following nonlimiting examples: colloidal gold (40-80 nm diameter), which scatters green light with high efficiency; fluorescent labels, such as fluorescein, Texas red, Rhoda mine, and green fluorescent protein (Molecular Probes, Eugene, Oreg.), which absorb and subsequently emit light; chemiluminescent or bioluminescent labels, such as luminol, lophine, acridine salts and luciferins, which are electronically excited as the result of a chemical or biological reaction and subsequently emit light; spin labels, such as vanadium, copper, iron, manganese and nitroxide free radicals, which are detected by electron spin resonance (ESR) spectroscopy; dyes, such as quinoline dyes, triarylmethane dyes and acridine dyes, which absorb specific wavelengths of light; and colored glass or plastic (e.g., polystyrene, polypropylene, latex, etc.) beads. See U.S. Pat. Nos. 3,817,837; 3,850,752; 3,939,350; 3,996,345; 4,277,437; 4,275,149 and 4,366,241.

A detectable moiety provides an indirect signal where it interacts with a second compound that spontaneously emits a signal, or generates a signal upon the introduction of a suitable stimulus. Biotin, for example, produces a signal by forming a conjugate with streptavidin, which is then detected. See Hybridization With Nucleic Acid Probes. In *Laboratory Techniques in Biochemistry and Molecular Biology;* Tijssen, P., Ed.; Elsevier: New York, 1993; Vol. 24. An enzyme, such as horseradish peroxidase or alkaline phosphatase, that is attached to an antibody in a label-antibody-antibody as in an ELISA assay, also produces an indirect signal.

A preferred detectable moiety is a fluorescent group. Fluorescent groups typically produce a high signal to noise ratio, thereby providing increased resolution and sensitivity in a detection procedure. Preferably, the fluorescent group absorbs light with a wavelength above about 300 nm, more preferably above about 350 nm, and most preferably above about 400 nm. The wavelength of the light emitted by the fluorescent group is preferably above about 310 nm, more preferably above about 360 nm, and most preferably above about 410 nm.

The fluorescent detectable moiety is selected from a variety of structural classes, including the following nonlimiting examples: 1- and 2-aminonaphthalene, p,p'diaminostilbenes, pyrenes, quaternary phenanthridine salts, 9-aminoacridines, p,p'-diaminobenzophenone imines, anthracenes, oxacarbocyanine, marocyanine, 3-aminoequilenin, perylene, bisbenzoxazole, bis-p-oxazolyl benzene, 1,2-benzophenazin, retinol, bis-3-aminopridinium salts, hellebrigenin, tetracycline, sterophenol, benzimidazolyl phenylamine, 2-oxo-3-chromen, indole, xanthen, 7-hydroxycoumarin, phenoxazine, salicylate, strophanthidin, porphyrins, triarylmethanes, flavin, xanthene dyes (e.g., fluorescein and rhodamine dyes); cyanine dyes; 4,4-difluoro-4-bora-3a,4a-diaza-s-indacene dyes and fluorescent proteins (e.g., green fluorescent protein, phycobiliprotein).

A number of fluorescent compounds are suitable for incorporation into the present invention. Nonlimiting examples of such compounds include the following: dansyl chloride; fluoresceins, such as 3,6-dihydroxy-9-phenylxanthhydrol; rhodamineisothiocyanate; N-phenyl-1-amino-8-sulfonatonaphthalene; N-phenyl-2-amino-6-sulfonatonaphthanlene; 4-acetamido-4-isothiocyanatostilbene-2,2'-disulfonic acid; pyrene-3-sulfonic acid; 2-toluidinonapthhalene-6-sulfonate; N-phenyl, N-methyl 2-aminonaphthalene-6-sulfonate; ethidium bromide; stebrine; auromine-0,2-(9'-anthroyl)palmitate; dansyl phosphatidylethanolamin; N,N'-dioctadecyl oxacarbocycanine; N,N'-dihexyl oxacarbocyanine; merocyanine, 4-(3'-pyrenyl) butyrate; d-3-aminodesoxy-equilenin; 12-(9'-anthroyl)stearate; 2-methylanthracene; 9-vinylanthracene; 2,2'-(vinylene-p-phenylene)bisbenzoxazole; p-bis[2-(4-methyl-5-phenyl oxazolyl)]benzene; 6-dimethylamino-1,2-benzophenzin; retinol; bis(3'-aminopyridinium)-1,10-decandiyl diiodide; sulfonaphthylhydrazone of hellibrienin; chlorotetracycline; N-(7-dimethylamino-4-methyl-2-oxo-3-chromenyl)maleimide; N-[p-(2-benzimidazolyl)phenyl]maleimide; N-(4-fluoranthyl)maleimide; bis(homovanillic acid); resazarin; 4-chloro-7-nitro-2,1,3-benzooxadizole; merocyanine 540; resorufin; rose bengal and 2,4-diphenyl-3(2H)-furanone. Preferably, the fluorescent detectable moiety is a fluorescein or rhodamine dye.

Another preferred detectable moiety is colloidal gold. The colloidal gold particle is typically 40 to 80 nm in diameter. The colloidal gold may be attached to a labeling compound in a variety of ways. In one embodiment, the linker moiety of the nucleic acid labeling compound terminates in a thiol group (—SH), and the thiol group is directly bound to colloidal gold through a dative bond. See Mirkin et al. *Nature* 1996, 382, 607-609. In another embodiment, it is attached indirectly, for instance through the interaction between colloidal gold conjugates of antibiotin and a biotinylated labeling compound. The detection of the gold labeled compound may be enhanced through the use of a silver enhancement method. See Danscher et al. *J. Histotech* 1993, 16, 201-207.

The term "effective amount" as used herein refers to an amount sufficient to induce a desired result.

Although generally used herein to define separate regions containing differing polymer sequences, the term "feature" generally refers to any element, e.g., region, structure or the like, on the surface of a substrate. Typically, substrates to be scanned, will have small feature sizes, and consequently, high feature densities on substrate surfaces. For example, individual features will typically have at least one of a length or width dimension that is no greater than 100 microns, and preferably, no greater than 50 microns, and more preferably no greater than about 20 microns. Thus, for embodiments employing substrates having a plurality of polymer sequences on their surfaces, each different polymer sequence will typically be substantially contained within a single feature.

The term "fragmentation" refers to the breaking of nucleic acid molecules into smaller nucleic acid fragments. In certain embodiments, the size of the fragments generated during fragmentation can be controlled such that the size of fragments is distributed about a certain predetermined nucleic acid length.

The term "genome" as used herein is all the genetic material in the chromosomes of an organism. DNA derived from the genetic material in the chromosomes of a particular organism is genomic DNA. A genomic library is a collection of clones made from a set of randomly generated overlapping DNA fragments representing the entire genome of an organism.

The term "hybridization" as used herein refers to the process in which two single-stranded polynucleotides bind non-covalently to form a stable double-stranded polynucleotide; triple-stranded hybridization is also theoretically possible. The resulting (usually) double-stranded polynucleotide is a "hybrid." The proportion of the population of polynucleotides that forms stable hybrids is referred to herein as the "degree of hybridization." Hybridizations are usually performed under stringent conditions, for example, at a salt concentration of no more than 1 M and a temperature of at least 25° C. For example, conditions of 5×SSPE (750 mM NaCl, 50 mM NaPhosphate, 5 mM EDTA, pH 7.4) and a temperature of 25-30° C. are suitable for allele-specific probe hybridizations. For stringent conditions, see, for example, Sambrook, Fritsche and Maniatis. "Molecular Cloning A laboratory Manual" $2^{nd}$ Ed. Cold Spring Harbor Press (1989) which is hereby incorporated by reference in its entirety for all purposes above.

The term "hybridization conditions" as used herein will typically include salt concentrations of less than about 1M, more usually less than about 500 mM and preferably less than about 200 mM. Hybridization temperatures can be as low as 5° C., but are typically greater than 22° C., more typically greater than about 30° C., and preferably in excess of about 37° C. Longer fragments may require higher hybridization temperatures for specific hybridization. As other factors may affect the stringency of hybridization, including base composition and length of the complementary strands, presence of organic solvents and extent of base mismatching, the combination of parameters is more important than the absolute measure of any one alone.

The term "hybridization probes" as used herein are oligonucleotides capable of binding in a base-specific manner to a complementary strand of nucleic acid. Such probes include peptide nucleic acids, as described in Nielsen et al., *Science* 254, 1497-1500 (1991), and other nucleic acid analogs and nucleic acid mimetics.

The term "hybridizing specifically to" as used herein refers to the binding, duplexing, or hybridizing of a molecule only to a particular nucleotide sequence or sequences under stringent conditions when that sequence is present in a complex mixture (for example, total cellular) DNA or RNA.

The term "initiation monomer" or "initiator monomer" as used herein is meant to indicate the first monomer which is covalently attached via reactive groups, e.g., nucleophiles and electrophiles to the surface of the polymer, or the first monomer which is attached to a linker or spacer arm attached to the polymer, the linker or spacer arm being attached to the polymer via reactive groups.

The term "isolated nucleic acid" as used herein mean an object species invention that is the predominant species present (i.e., on a molar basis it is more abundant than any other individual species in the composition). Preferably, an isolated nucleic acid comprises at least about 50, 80 or 90% (on a molar basis) of all macromolecular species present. Most preferably, the object species is purified to essential homogeneity (contaminant species cannot be detected in the composition by conventional detection methods).

The term "ligand" as used herein refers to a molecule that is recognized by a particular receptor. The agent bound by or reacting with a receptor is called a "ligand," a term which is definitionally meaningful only in terms of its counterpart receptor. The term "ligand" does not imply any particular molecular size or other structural or compositional feature other than that the substance in question is capable of binding or otherwise interacting with the receptor. Also, a ligand may serve either as the natural ligand to which the receptor binds, or as a functional analogue that may act as an agonist or antagonist. Examples of ligands that can be investigated by this invention include, but are not restricted to, agonists and antagonists for cell membrane receptors, toxins and venoms, viral epitopes, hormones (for example, opiates, steroids, etc.), hormone receptors, peptides, enzymes, enzyme substrates, substrate analogs, transition state analogs, cofactors, drugs, proteins, and antibodies.

The term "linkage disequilibrium" or sometimes refer by allelic association as used herein refers to the preferential association of a particular allele or genetic marker with a specific allele, or genetic marker at a nearby chromosomal location more frequently than expected by chance for any particular allele frequency in the population. For example, if locus X has alleles a and b, which occur equally frequently, and linked locus Y has alleles c and d, which occur equally frequently, one would expect the combination ac to occur with a frequency of 0.25. If ac occurs more frequently, then alleles a and c are in linkage disequilibrium. Linkage disequilibrium may result from natural selection of certain combination of alleles or because an allele has been introduced into a population too recently to have reached equilibrium with linked alleles.

The term "mixed population" or sometimes refer by "complex population" as used herein refers to any sample containing both desired and undesired nucleic acids. As a non-limiting example, a complex population of nucleic acids may be total genomic DNA, total genomic RNA or a combination thereof. Moreover, a complex population of nucleic acids may have been enriched for a given population but include other undesirable populations. For example, a complex population of nucleic acids may be a sample which has been enriched for desired messenger RNA (mRNA) sequences but still includes some undesired ribosomal RNA sequences (rRNA).

The term "monomer" as used herein refers to any member of the set of molecules that can be joined together to form an oligomer or polymer. The set of monomers useful in the present invention includes, but is not restricted to, for the example of (poly)peptide synthesis, the set of L-amino acids, D-amino acids, or synthetic amino acids. As used herein, "monomer" refers to any member of a basis set for synthesis of an oligomer. For example, dimers of L-amino acids form a basis set of 400 "monomers" for synthesis of polypeptides. Different basis sets of monomers may be used at successive steps in the synthesis of a polymer. The term "monomer" also refers to a chemical subunit that can be combined with a different chemical subunit to form a compound larger than either subunit alone.

The term "mRNA," or sometimes referred to as "mRNA transcripts," as used herein, includes, but not limited to pre-mRNA transcript(s), transcript processing intermediates, mature mRNA(s) ready for translation and transcripts of the gene or genes, or nucleic acids derived from the mRNA transcript(s). Transcript processing may include splicing, editing and degradation. As used herein, a nucleic acid derived from an mRNA transcript refers to a nucleic acid for whose synthesis the mRNA transcript or a subsequence thereof has ultimately served as a template. Thus, a cDNA reverse transcribed from an mRNA, an RNA transcribed from that cDNA, a DNA amplified from the cDNA, an RNA transcribed from the amplified DNA, etc., are all derived from the mRNA transcript and detection of such derived products is indicative of the presence and/or abundance of the original transcript in a sample. Thus, mRNA derived samples include, but are not limited to, mRNA transcripts of the gene or genes, cDNA reverse transcribed from the mRNA, cRNA transcribed from the cDNA, DNA amplified from the genes, RNA transcribed from amplified DNA, and the like.

The term "nucleic acid library" or sometimes refer by "array" as used herein refers to an intentionally created collection of nucleic acids which can be prepared either synthetically or biosynthetically and screened for biological activity in a variety of different formats (for example, libraries of soluble molecules; and libraries of oligos tethered to resin beads, silica chips, or other solid supports). Additionally, the term "array" is meant to include those libraries of nucleic acids which can be prepared by spotting nucleic acids of essentially any length (for example, from 1 to about 1000 nucleotide monomers in length) onto a substrate. The term "nucleic acid" as used herein refers to a polymeric form of nucleotides of any length, either ribonucleotides, deoxyribonucleotides or peptide nucleic acids (PNAs), that comprise purine and pyrimidine bases, or other natural, chemically or biochemically modified, non-natural, or derivatized nucleotide bases. The backbone of the polynucleotide can comprise sugars and phosphate groups, as may typically be found in RNA or DNA, or modified or substituted sugar or phosphate groups. A polynucleotide may comprise modified nucleotides, such as methylated nucleotides and nucleotide analogs. The sequence of nucleotides may be interrupted by non-nucleotide components. Thus the terms nucleoside, nucleotide, deoxynucleoside and deoxynucleotide generally include analogs such as those described herein. These analogs are those molecules having some structural features in common with a naturally occurring nucleoside or nucleotide such that when incorporated into a nucleic acid or oligonucleoside sequence, they allow hybridization with a naturally occurring nucleic acid sequence in solution. Typically, these analogs are derived from naturally occurring nucleosides and nucleotides by replacing and/or modifying the base, the ribose or the phosphodiester moiety. The changes can be tailor made to stabilize or destabilize hybrid formation or enhance the specificity of hybridization with a complementary nucleic acid sequence as desired.

The term "nucleic acids" as used herein may include any polymer or oligomer of pyrimidine and purine bases, preferably cytosine, thymine, and uracil, and adenine and guanine, respectively. See Albert L. Lehninger, PRINCIPLES OF BIOCHEMISTRY, at 793-800 (Worth Pub. 1982). Indeed, the present invention contemplates any deoxyribonucleotide, ribonucleotide or peptide nucleic acid component, and any chemical variants thereof, such as methylated, hydroxymethylated or glucosylated forms of these bases, and the like. The polymers or oligomers may be heterogeneous or homogeneous in composition, and may be isolated from naturally-occurring sources or may be artificially or synthetically produced. In addition, the nucleic acids may be DNA or RNA, or a mixture thereof, and may exist permanently or transitionally in single-stranded or double-stranded form, including homoduplex, heteroduplex, and hybrid states.

The term "PVP" refers to polyvinylpyrrolidone, which has the structure:

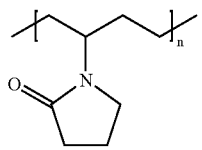

The term "oligonucleotide" or sometimes refer by "polynucleotide" as used herein refers to a nucleic acid ranging from at least 2, preferable at least 8, and more preferably at least 20 nucleotides in length or a compound that specifically hybridizes to a polynucleotide. Polynucleotides of the present invention include sequences of deoxyribonucleic acid (DNA) or ribonucleic acid (RNA) which may be isolated from natural sources, recombinantly produced or artificially synthesized and mimetics thereof. A further example of a polynucleotide of the present invention may be peptide nucleic acid (PNA). The invention also encompasses situations in which there is a nontraditional base pairing such as Hoogsteen base pairing which has been identified in certain tRNA molecules and postulated to exist in a triple helix. "Polynucleotide" and "oligonucleotide" are used interchangeably in this application.

The term "polymorphism" as used herein refers to the occurrence of two or more genetically determined alternative sequences or alleles in a population. A polymorphic marker or site is the locus at which divergence occurs. Preferred markers have at least two alleles, each occurring at frequency of greater than 1%, and more preferably greater than 10% or 20% of a selected population. A polymorphism may comprise one or more base changes, an insertion, a repeat, or a deletion. A polymorphic locus may be as small as one base pair. Polymorphic markers include restriction fragment length polymorphisms, variable number of tandem repeats (VNTR's), hypervariable regions, minisatellites, dinucleotide repeats, trinucleotide repeats, tetranucleotide repeats, simple sequence repeats, and insertion elements such as Alu. The first identified allelic form is arbitrarily designated as the reference form and other allelic forms are designated as alternative or variant alleles. The allelic form occurring most frequently in a selected population is sometimes referred to as the wildtype form. Diploid organisms may be homozygous or heterozygous for allelic forms. A diallelic polymorphism has two forms. A triallelic polymorphism has three forms. Single nucleotide polymorphisms (SNPs) are included in polymorphisms.

The term "primer" as used herein refers to a single-stranded oligonucleotide capable of acting as a point of initiation for template-directed DNA synthesis under suitable conditions for example, buffer and temperature, in the presence of four different nucleoside triphosphates and an agent for polymerization, such as, for example, DNA or RNA polymerase or reverse transcriptase. The length of the primer, in any given case, depends on, for example, the intended use of the primer, and generally ranges from 15 to 30 nucleotides. Short primer molecules generally require cooler temperatures to form sufficiently stable hybrid complexes with the template. A primer need not reflect the exact sequence of the template but must be sufficiently complementary to hybridize with such template. The primer site is the area of the template to which a primer hybridizes. The primer pair is a set of primers including a 5' upstream primer that hybridizes with the 5' end of the sequence to be amplified and a 3' downstream primer that hybridizes with the complement of the 3' end of the sequence to be amplified.

The term "probe" as used herein refers to a surface-immobilized molecule that can be recognized by a particular target. See U.S. Pat. No. 6,582,908 for an example of arrays having all possible combinations of probes with 10, 12, and more bases. Examples of probes that can be investigated by this invention include, but are not restricted to, agonists and antagonists for cell membrane receptors, toxins and venoms, viral epitopes, hormones (for example, opioid peptides, steroids, etc.), hormone receptors, peptides, enzymes, enzyme substrates, cofactors, drugs, lectins, sugars, oligonucleotides, nucleic acids, oligosaccharides, proteins, and monoclonal antibodies.

The term "receptor" as used herein refers to a molecule that has an affinity for a given ligand. Receptors may be naturally-occurring or manmade molecules. Also, they can be employed in their unaltered state or as aggregates with other species. Receptors may be attached, covalently or noncovalently, to a binding member, either directly or via a specific binding substance. Examples of receptors which can be employed by this invention include, but are not restricted to, antibodies, cell membrane receptors, monoclonal antibodies and antisera reactive with specific antigenic determinants (such as on viruses, cells or other materials), drugs, polynucleotides, nucleic acids, peptides, cofactors, lectins, sugars, polysaccharides, cells, cellular membranes, and organelles. Receptors are sometimes referred to in the art as anti-ligands. As the term receptors is used herein, no difference in meaning is intended. A "Ligand Receptor Pair" is formed when two macromolecules have combined through molecular recognition to form a complex. Other examples of receptors which can be investigated by this invention include but are not restricted to those molecules shown in U.S. Pat. No. 5,143,854, which is hereby incorporated by reference in its entirety.

The term "solid support", "support", and "substrate" as used herein are used interchangeably and refer to a material or group of materials having a rigid or semi-rigid surface or surfaces. In many embodiments, at least one surface of the solid support will be substantially flat, although in some embodiments it may be desirable to physically separate synthesis regions for different compounds with, for example, wells, raised regions, pins, etched trenches, or the like. According to other embodiments, the solid support(s) will take the form of beads, resins, gels, microspheres, or other geometric configurations. See U.S. Pat. No. 5,744,305 for exemplary substrates.

The term "target" as used herein refers to a molecule that has an affinity for a given probe. Targets may be naturally-occurring or man-made molecules. Also, they can be employed in their unaltered state or as aggregates with other species. Targets may be attached, covalently or noncovalently, to a binding member, either directly or via a specific binding substance. Examples of targets which can be employed by this invention include, but are not restricted to, antibodies, cell membrane receptors, monoclonal antibodies and antisera reactive with specific antigenic determinants (such as on viruses, cells or other materials), drugs, oligonucleotides, nucleic acids, peptides, cofactors, lectins, sugars, polysaccharides, cells, cellular membranes, and organelles. Targets are sometimes referred to in the art as anti-probes. As the term targets is used herein, no difference in meaning is intended. A "Probe Target Pair" is formed when two macromolecules have combined through molecular recognition to form a complex.

C. Platform for Label Free Analysis of Genomic DNA

In accordance with an aspect of the present invention, the platform for label free analysis of genomic DNA analysis relates generally to diagnostic and genomic analysis. An aspect of the present invention contemplates the use of a polymeric matrix and its use as a platform for label free analysis of genomic material. As is known to those of skill in the a great deal of time and effort has gone into the preparation, standardization, etc. for labels for the detection of genomic DNA and mRNA. While many successful labels have been created, it is not without cost. Indeed, labeling technology has become a significant amount of the expense of running a nucleic acid array analysis.

The present invention relates to the use of polymeric matrices and their use as a platform for label free analysis of genomic material. These matrices comprise a fluorescent substrate that can be used as a support for DNA synthesis. This DNA/RNA layer has the effect of changing the emission intensity of the fluorescent substrate. Hybridization of the DNA/RNA material will cause a further change in emission intensity, and therefore a recordable signal to be used for the genomic analysis (Scheme 1).

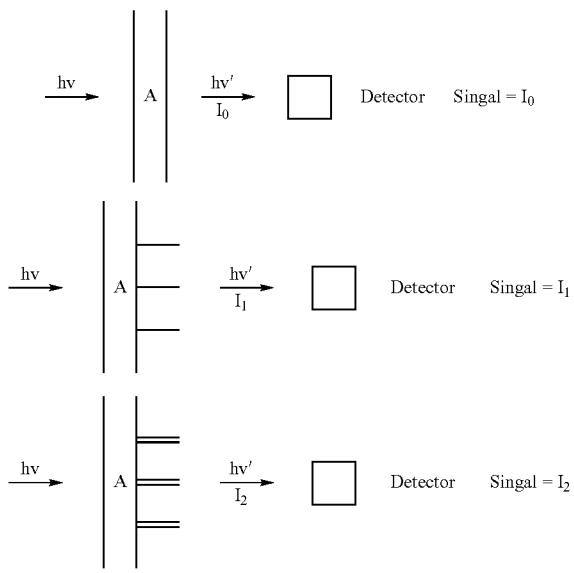

Scheme I. Platform for label free analysis of genomic material.

In accordance with an aspect of the present invention, it is postulated that the mechanism of change in emission intensity I upon hybridization is due to the change in refractive index of the medium ($\eta$) experienced by the emitted light before reaching the detector. The emission intensity is proportional to the optical density at the excitation wavelength (OD), the quantum efficiency of the emitting species ($\Phi$) and inversely proportional to the square of the refractive index of the medium ($\eta$), equation 1.

$$I = \frac{OD\Phi}{\eta^2}$$

Equation I. Relationship between emission intensity and refractive index.

The DNA/RNA layer will result into a change of the refractive index and therefore into a change in the emission intensity (I), Scheme 2.

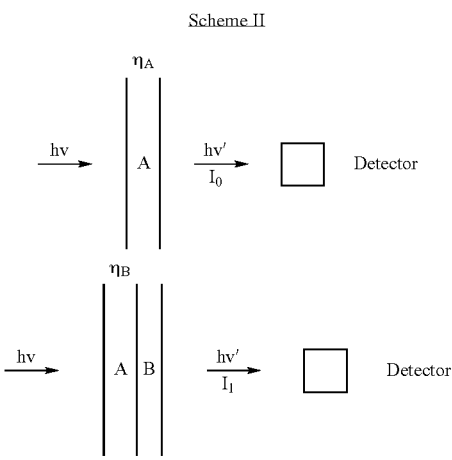

Scheme II

In accordance with an aspect of the present invention, several matrices may be useful to this purpose. In general the matrices could be either fluorescent of made fluorescent by doping or covalently attaching a fluorescent substrate.

EXAMPLE

As a preliminary result a fluorescent film (PVP-co-poly (N-2-methacryloxyethyl)methacrylamide attached to a 3-acryloxypropryl trimethoxysilane (or a 3-acrylamidopropyltrimethoxysilane) coated glass surface by spin-coating and phtopolymerizing at 254 nm) was used as a matrix for the label free analysis of genomic DNA. The film itself had a fluorescence of I=4,000 counts. When a layer of DNA was generated onto the surface, using Menpoc-amidites, the fluorescence intensity increased to 8,000 counts. When a layer of DNA was generated onto the polymer, but with TCA chemistry, a more efficient chemistry, a larger signal was recorded I=12,000 counts. Finally the probe was exposed to the specific unlabeled target and let to hybridize at room temperature for, it resulted in a further increase of the emission intensity (I=15,000 counts after only 1 hour, I=20,000 counts after 17 hours.

It is to be understood that the above description is intended to be illustrative and not restrictive. Many variations of the invention will be apparent to those of skill in the art upon reviewing the above description. All cited references, including patent and non-patent literature, are incorporated herein by reference in their entireties for all purposes.

What is claimed is:
1. A method for detecting nucleic acid hybridization without the use of a labeled probe, comprising:
   providing a fluorescent polymeric matrix having a first fluorescent emission intensity;
   attaching a single stranded DNA or RNA species to said fluorescent matrix to provide a second, greater fluorescent intensity; and
   hybridizing said single stranded RNA or DNA to a homologous nucleic acid, causing a further increase in said fluorescent intensity, allowing detection of said hybridization of said homologous nucleic acids.

2. The method of claim 1, wherein said fluorescent polymeric matrix comprises a polyvinylpyrrolidone (PVP).

3. The method of claim 1, wherein said fluorescent polymeric matrix comprises a fluorescent film.

4. The method of claim 3, wherein said fluorescent film is a PVP-co-poly(N-2-methacryloxyethyl)methacrylamide.

5. The method of claim 3, wherein said fluorescent film is attached to a 3-acryloxypropryl trimethoxysilane coated surface.

6. The method of claim 3, wherein said fluorescent film is attached to a 3-acrylamidopropyltrimethoxysilane coated surface.

7. The method of claim 4, wherein said PVP-co-poly(N-2-methacryloxyethyl)methacrylamide is attached to a 3-acryloxypropryl trimethoxysilane coated surface.

8. The method of claim 4, wherein said PVP-co-poly(N-2-methacryloxyethyl)methacrylamide is attached to a 3-acrylamidopropyltrimethoxysilane coated surface.

9. The method of claim 1, wherein the fluorescent polymeric matrix is on a solid substrate.

10. The method of claim 9, wherein the solid substrate is an array.

11. The method of claim 10, wherein the solid substrate is glass.

12. A method for detecting nucleic acid hybridization without a labeled probe, comprising:
hybridizing a nucleic acid molecule to a single stranded RNA or DNA species attached to a solid substrate,
wherein the surface of the solid substrate comprises a fluorescent polymeric matrix and
wherein hybridizing the nucleic acid molecule to the single stranded RNA or DNA causes an increase in fluorescent activity over the fluorescent activity of the polymeric matrix and the polymeric matrix to which the single stranded RNA or DNA is attached.

13. The method of claim 12, wherein said fluorescent polymeric matrix comprises a polyvinylpyrrolidone (PVP).

14. The method of claim 12, wherein said fluorescent polymeric matrix comprises a fluorescent film.

15. The method of claim 14, wherein said fluorescent film is a PVP-co-poly(N-2-methacryloxyethyl)methacrylamide.

16. The method of claim 14, wherein said fluorescent film is attached to a 3-acryloxypropryl trimethoxysilane coated surface.

17. The method of claim 14, wherein said fluorescent film is attached to a 3-acrylamidopropyltrimethoxysilane coated surface.

18. The method of claim 15, wherein said PVP-co-poly(N-2-methacryloxyethyl)methacrylamide is attached to a 3-acryloxypropryl trimethoxysilane coated surface.

19. The method of claim 15, wherein said PVP-co-poly(N-2-methacryloxyethyl)methacrylamide is attached to a 3-acrylamidopropyltrimethoxysilane coated surface.

20. The method of claim 1, wherein the fluorescent polymeric matrix is on a solid substrate.

21. The method of claim 20, wherein the solid substrate is an array.

22. The method of claim 21, wherein the solid substrate is glass.

* * * * *